United States Patent [19]
Majetich et al.

[11] Patent Number: 5,808,115
[45] Date of Patent: Sep. 15, 1998

[54] CARBODIIMIDE-PROMOTED EPOXIDATION OF OLEFINS

[75] Inventors: George F. Majetich; Rodgers Hicks, both of Athens, Ga.

[73] Assignee: University of Georgia Research Foundation, Athens, Ga.

[21] Appl. No.: 813,039

[22] Filed: Mar. 6, 1997

Related U.S. Application Data

[60] Provisional application No. 60/013,031, Mar. 8, 1996
[51] Int. Cl.$^6$ .................................................. C07D 301/12
[52] U.S. Cl. ............................................. 549/531
[58] Field of Search ............................................. 549/531

[56] References Cited

U.S. PATENT DOCUMENTS

| | | | |
|---|---|---|---|
| 4,471,130 | 9/1984 | Katsuki et al. | 549/523 |
| 4,594,439 | 6/1986 | Katsuki et al. | 549/523 |

OTHER PUBLICATIONS

Payne, G. et al. (1961), "Reactions of Hydrogen Peroxide. VII. Alkali–Catalyzed Epoxidation and Oxidation Using a Nitrile as Co–reactant," *J. Org. Chem.* 26:659–663.

Venturello, C. et al. (1983), "A New, Effective Catalytic System of Epoxidation of Olefins by Hydrogen Peroxide under Phase–Transfer Conditions," *J. Org. Chem.* 48:3831–3833.

Reynaud et al. (1985), "A Very Efficient System for Alkene Epoxidation by Hydrogen Peroxide: Catalysis by Manganese–Porphyrins in the Presence of Imidazole," *J. Chem. Soc. Chem. Commun.*, pp. 888–889.

Rebek, J., Jr. and McCready, R. (1979), "A New Class of Epoxidation Reagents," *Tet. Lett.* No. 12, pp. 1001–1002.

Rebek, J., Jr. and McCready, R. (1980), "Intramolecular epoxidation with the hydrogen peroxide/orthoester system" *Tet. Lett.* 21(26):2491–2492.

Rebek, J., Jr. and McCready, R. (1979), "New Epoxidation Reagents Dervied from Alumina and Silicon," *Tet. Lett.* No. 45, pp. 4337–4338.

Rebek, J., Jr. et al. (1980), "Olefin Epoxidation with α–Hydroperoxides of Esters, Amides, Ketones, and Nitriles," *J. Chem. Soc. Chem. Commun.*, pp. 705–706.

Heggs, R. and Ganem, B. (1979), "2–Hydroperoxyhexafluoro–2–propanol. A Low–Cost, Catalytic Oxidant for Synthesis and a Structural Analogue of Naturally Occurring Flavin Hydroperoxides," *J. Am. Chem. Soc.* 101:2484–2486.

Chen, Y. and Reymond, J.–L. (1995), "Epoxidation of Olefins with Formamide—Hydrogen Peroxide," *Tet. Let.* 36(23):4015–4018.

Krishnan, S. (1977), "The Formation of Arene Oxides by Direct Oxidation of Arenes Using Carbodiimides and Hydrogen Peroxide," *Tet. Lett.* No. 16, pp. 1369–1372.

Rebek, J., Jr. et al. (1974), "Substituted Peroxycarbamic Acids as Epoxidizing Agents," *J. Chem. Soc. Chem. Commun.*, p. 711.

Matsumura et al. (1970), "Epoxidation of Olefins with Hydrogen Peroxide Using an Isocyanate as Co–reactant," *Tet. Lett.* No. 23, pp. 2029–2032.

Rebek, J., et al., (1976), "Epoxidation and Singlet Oxygen Generation From Dehydrating Agents and Hydrogen Peroxide," *Abstracts of the 172nd National Meeting of the American Chemical Society*, ORGN 109.

Rebek et al. (1979), "New Oxidizing Agents from the Dehydration of Hydrogen Peroxide,"*J. Org. Chem.* 44(9):1485–1493.

Adamczyk et al. (1995), "An Easy Preparation of Hapten Active Esters via Solid Supported EDAC," *Tet. Lett.* 36(46):8345–8346.

Desai, M. and Stramiello, L. (1993), "Polymer Bound EDC (P–EDC): A Convenient Reagent for Formation of an Amide Bond," *Tet. Lett.*, 34(48):7685–7688.

Henbest, H.B.; Wilson, R.A.L. (1957), "Aspects of Stereochemistry. Part I. Stereospecificity in Formation of Epoxides from Cyclic Allylic Alcohols," *J. Chem. Soc.,* pp. 1958–1965.

March *Advanced Organic Chemistry,* 4th ed. Wiley, NY, (1992), pp. 826–829.

Garside, P. et al. (1969), "Action of Peracetic Acid on (+) Sabinol," J. Chem. Soc. C, pp. 716–721.

Majetich, G. and Hicks, R. (1995), "Carbodiimide Mediated Epoxidation of Olefins with Aqueous Hydrogen Peroxide," Thirty–Fourth Natl. Organic Symp., The College of William and Mary, Williamsburg, Virginia, Jun. 11–15, 1995, Abstract #80.

Wolf, S.F., (1977), "Epoxidation and Singlet Oxygen Generation from Dehydrating Agents and Hydrogen Peroxide," Ph.D. Thesis, University of California, Los Angeles.

*Primary Examiner*—Ba K. Trinh
*Attorney, Agent, or Firm*—Greenlee, Winner & Sullivan, P.C.

[57] ABSTRACT

A method is provided for oxidizing an olefin to an epoxide by treating the olefin with hydrogen peroxide and a carbodiimide in the presence of an acid or base in a solvent system comprising a protic solvent. More specifically, a method is provided for oxidizing an olefin to an epoxide by contacting the olefin with aqueous hydrogen peroxide and a carbodiimide in the presence of a mild acid or mild base in a solvent system comprising a protic solvent.

29 Claims, No Drawings

CARBODIIMIDE-PROMOTED EPOXIDATION OF OLEFINS

BACKGROUND OF THE INVENTION

CROSS-REFERENCED TO RELATED APPLICATIONS

This application takes priority from U.S. provisional application Ser. No. 60/013,031, filed Mar. 8, 1996.

FIELD OF THE INVENTION

This invention relates generally to organic chemistry and more specifically to a method for preparing epoxides from olefins. The epoxidation can be made to be stereoselective.

BACKGROUND OF THE INVENTION

The epoxidation of olefins is a fundamental industrial process. Organic chemists have tried for years to effect epoxidation of simple, unactivated alkenes with aqueous hydrogen peroxide because it gives only water as a by-product and is both economical and readily available.

It is known that some olefins can be epoxidized by dilute solution of hydrogen peroxide, but that the addition of a nitrile (Payne, G. et al., *J. Org. Chem.* 1961, 26, 659) ; a pertungstate salt (Venturello, C. et al., *J. Org. Chem.* 1983, 48, 3831) ; a metallo-porphyrin (Reynaud et al., *J. Chem. Soc. Chem. Commun.* 1985, 888); an α-hydroperoxycarbonyl-compound (Rebec, J., Jr. and McCready, R., *Tet. Lett.* 1979, 1001, 2491, 4337; Rebec, J., Jr. and McCready, R., *J. Chem. Soc. Chem. Commun.* 1980, 705; Heggs, R. and Ganem, B., *J. Am. Chem. Soc.* 1979, 101, 2484); or a formamide (Chen, Y. and Reymond, J.-L., *Tet. Let.* (1995) 36(23):4015), increases the efficiency of epoxidation. The Sharpless Asymmetric Epoxidation uses a metal and an asymmetric alkoxide catalyst to asymmetrically epoxidize many olefins (U.S. Pat. No. 4,594,439 and U.S. Pat. No. 4,471,130).

Anhydrous hydrogen peroxide (98%) and carbodiimides were used in acidic ethyl acetate, an aprotic solvent, to epoxidize two arenes, phenanthrene and pyrene, but only in about 3% yield, based on the initial amount of the arene (Hamilton et al., *Tet. Lett,* 1977, 16, 1369). For example, phenanthrene (4 mmol), diisopropylcarbodiimide (8 mmol), 98% hydrogen peroxide (16 mmol), and acetic acid (8 mmol) were reacted in ethyl acetate. The yield of phenanthrene 9, 10-oxide was 28% based on the amount of reacted phenanthrene and 2.9% based on the amount of phenanthrene initially present. A reaction of pyrene under similar conditions yielded pyrene 4,5-oxide in 27% yield, based on the amount of reacted pyrene; the yield based on the amount of pyrene initially present was not stated. These researchers state that, "Control experiments indicate that all four components (arene, carbodiimide, $H_2O_2$, and acid) are required for the reaction." They also state that approximately the same yield of oxide is formed from these arenes when 30% hydrogen peroxide, and a four-fold increase in the carbodiimide concentration, are used instead of 98% hydrogen peroxide. The authors also speculate that, "In addition to its use in arene oxide synthesis, the carbodiimide-$H_2O_2$ system may be useful for simple alkene epoxidations under mild conditions," and make reference to three earlier articles. Two of the references cited by the authors, however, refer to systems using reagents other than carbodiimides to effect epoxidation of olefins. One reference cited (Rebek, J., Jr. et al., *J. Chem. Soc. Chem. Commun.*, 1974, 711) reports that substituted peroxycarbamic acids, generated in situ from anhydrous hydrogen peroxide and carbonyldiimidazole, can be used to epoxidize olefins. A second reference cited (Matsumura et al. Tet. Lett. 1970, 2029.) reports that reaction of an isocyanate and hydrogen peroxide, in the presence of an olefin, leads to epoxidation of olefins.

The third reference cited (Rebek, J., et al., *ABSTRACTS of the 172nd National Meeting of the American Chemical Society*, ORGN 109 1976) reports that olefins treated with carbodiimides and concentrated hydrogen peroxide produce epoxides in good yields. However, a later manuscript by the same authors (Rebek et al., *J. Org. Chem.* 1979, 44, 1485) reported that anhydrous hydrogen peroxide (an ethereal solution, 4M) in combination with carbodiimides failed to oxidize olefins to epoxides. The authors state that, "The commercially available dicyclohexylcarbodiimide (DCC) failed to epoxidize cyclododecenes in THF containing $H_2O_2$ even when acidic (HCl or $HBF_4$) or basic ($NaHCO_3$) catalysts were present. Acetic or, better, trifluoroacetic acids were effective epoxidation catalysts, but it is likely that the actual epoxidizing agents in these cases were the corresponding peracids. Further, epoxidation ceased after a few turnovers with these 'catalysts' and acylureas could be found in the reaction mixture."

The present invention differs from all of the above because it provides a method for oxidizing olefins to epoxides, including acid-sensitive epoxides, in good yields, using hydrogen peroxide and carbodiimide in a solvent system comprising a protic solvent with either an acid or base reagent included. This invention is useful in the chemical manufacturing and pharmaceutical industries. The method provided for preparing epoxides has many advantages over other methods for epoxidizing olefins. It employs a safe, economical, and readily available oxidizing agent, hydrogen peroxide, in combination with readily available and recyclable carbodiimide reagents, yet gives yields comparable to those obtained with harsher methods. The reagents utilized in the reactions of the present invention are generally less hazardous than reagents used in other methods to epoxidize olefins. The urea by-product of epoxidation is safe, easily removed, and can be regenerated to carbodiimide. The present invention, employing a mild acid or base, avoids the undesired by-products of prior art epoxidations. For example, the present invention can be used to epoxidize substrates containing carbonyl functionalities without undesired Baeyer-Villiger oxidation occurring, under either basic or acidic conditions.

SUMMARY OF THE INVENTION

A method is provided for oxidizing an olefin to an epoxide by treating the olefin with hydrogen peroxide and a carbodiimide in the presence of an acid or base in a solvent system comprising a protic solvent.

More specifically, a method is provided for oxidizing an olefin to an epoxide by contacting the olefin with aqueous hydrogen peroxide and a carbodiimide in the presence of a mild acid or mild base in a solvent system comprising a protic solvent.

For the present invention, an aqueous 30% hydrogen peroxide solution is preferred. The reaction, however, does not require the presence of water. The preferred solvents are simple alcohols, particularly ethanol and methanol. Preferred carbodiimides are dicyclohexylcarbodiimide, N,N'-diisopropylcarbodiimide, and 1-ethyl-3-(3-dimethylaminopropyl)carbodiimide. Sodium bicarbonate or a mild cationic exchange resin are preferred base or acid, respectively, in the present invention.

DESCRIPTION OF THE SPECIFIC EMBODIMENTS

In the method of the invention, a carbodiimide and hydrogen peroxide are used to transfer an oxygen to an olefin in the presence of acid or base in a solvent system comprising protic solvent.

The term "protic solvent" as used herein means solvent containing hydrogen that is attached to oxygen and is acidic enough to form hydrogen bonds. Protic solvents useful for the reaction of this invention are hydroxylic, that is, they contain a hydroxyl (—OH) group. Herein the term "protic solvent" also includes water, mixtures of alcohols, and aqueous mixtures. Simple alkyl alcohols, including methanol, ethanol, n-propanol, isopropyl alcohol, n-butanol, isobutyl alcohol, sec-butyl alcohol, tert-butyl alcohol, n-pentanol, isopentyl alcohol, tert-pentyl alcohol, neopentyl alcohol, n-hexanol, isohexyl alcohol, neohexyl alcohol, 5-methyl-1-hexanol, 1-methyl-1-pentanol, 1-ethyl-1-butanol, 2-methyl-1-pentanol, 2-ethyl-1-butanol, 3-methyl-1-pentanol are useful protic solvents. Preferred protic solvents for this invention are shorter chain alcohols: methanol, ethanol, n-propanol, iso-propanol, n-butanol, iso-butyl alcohol, sec-butyl alcohol and t-butyl alcohol. Solvent mixtures of simple alcohols with longer chain alcohols or aryl substituted alcohols like phenol or benzyl alcohol are also useful for the reaction of this invention. Methanol and ethanol are most preferred solvents. Amines, such as triethyl amine and diisopropyl amine, are not useful protic solvents for the reaction of this invention.

The invention employs solvent systems which comprise protic solvent. The reaction solvent must have some protic component. The solvent can, however, be anhydrous. A solvent that is substantially protic, as used herein, is one which comprises 50% or more by volume of one or more protic solvents. Preferred protic solvent systems are those which are substantially protic. The solvent system used in the reaction of this invention may be a mixture of protic solvent components, and optionally can contain aprotic solvent. The solvent system is preferably a single phase system. Solvent system components are chosen to dissolve, or at least partially dissolve, the reactant olefin and to maximize yield of desired epoxide. The solvent system for the reactions of this invention preferably is substantially protic and preferably also contains water. Aprotic solvents may be added to enhance solubility of reactants. Addition of aprotic solvents may, however, decrease reaction rate and/or yield. Heating those reactions using a mixture of protic and aprotic solvent can enhance yield or rate of reaction. Solvents employed should not themselves chemically react with carbodiimides or hydrogen peroxide.

Without being bound by any particular theory, it is believed that the invention is based on the following mechanism:

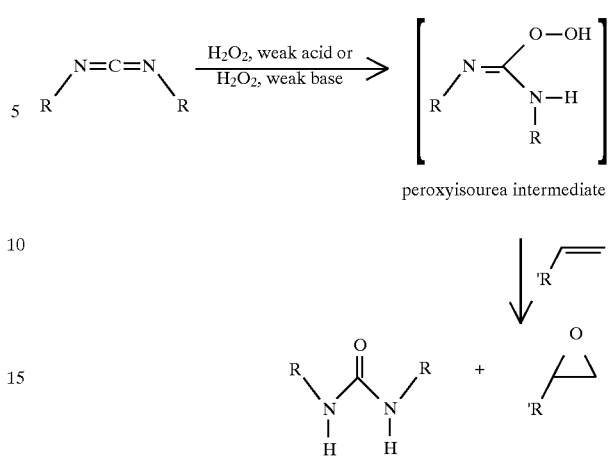

peroxyisourea intermediate

Hydrogen peroxide under acidic conditions, or hydroperoxide anion under basic conditions, nucleophilically attacks a carbodiimide, forming a peroxyisourea intermediate. This intermediate then transfers oxygen in a concerted fashion to the double bond of the substrate, in the same way in which peroxyacids and peroxycarboximidic acids do. Protic solvent is believed necessary to solvate and stabilize the peroxyisourea intermediate.

The carbodiimide may be either water soluble or organic soluble. Examples of commercially available carbodiimides are: dicyclohexylcarbodiimide (DCC); N,N'-diisopropylcarbodiimide (DIC); and 1-ethyl-3-(3-dimethylaminopropyl)carbodiimide (EDC); N,N'-dicyclohexylcarbodiimide methiode; N,N'-dicyclohexylcarbodiimide pentachlorophenol; N,N'-di-tert-butylcarbodiimide; N,N'-di-p-tolylcarbodiimide; N-cyclohexyl-N'-(1-pyrenyl)carbodiimide; diethylcarbodiimide. DCC, DIC, and EDC are preferred carbodiimides. DCC is the least expensive of these; DIC is a liquid and therefore very easy to handle; and EDC is water soluble. For ease of purification and regeneration, the carbodiimide can be bound to a polymer (Adamczyk et al., Tet. Lett. 1995, 36, 8345; Desai, M. and Stamiello, L., Tet. Lett. 1993, 34, 7685). After use, the carbodiimide can be regenerated by standard methods for dehydrating N, N-disubstituted ureas to carbodiimides. The carbodiimide has the general formula:

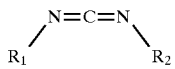

$R_1$ and $R_2$ are selected from in the group: alkyl, amino alkyl, alkenyl, cycloalkyl, and aryl. Those of ordinary skill in the art can chose from among the various carbodiimides available commercially or by routine synthesis, a carbodiimide for particular reaction conditions.

The hydrogen peroxide is preferably aqueous, containing about 1% to 99% water. Hydrogen peroxide containing about 2% to 97% water can be used. Hydrogen peroxide containing about 50% to 90% water can be used. An aqueous solution of 30% hydrogen peroxide which is readily available commercially is preferred. Using a large excess of 30% hydrogen peroxide, about five to ten mole equivalents, compared to carbodiimide improves the rate of reaction.

In general, this reaction will epoxidize any olefin except enones. The reason enones are not good substrates for the reaction of this invention is that under basic conditions hydroperoxide anion rapidly nucleophilically attacks the electron-deficient enone in a Michael-addition reaction. The enone is epoxidized under these conditions, but the reaction does not involve the carbodiimide and is not believed to involve the peroxyisourea intermediate.

Furthur fused aromatic compounds are not good substrates for the reaction of this invention. The reason fused aromatic compounds are not good substrates for this reaction is believed to be a combination of their insolubility in protic, simple alcohol solvent and the unfavorable thermodynamics of destroying aromaticity via epoxidation.

The reaction of this invention is particularly effective for epoxidation of olefins which generate sensitive epoxides, which may decompose under the reaction conditions used by other methods. For example, the epoxide of β-pinene is too acid-sensitive to be prepared using m-chloroperbenzoic acid (mCPBA), but is easily prepared by the reaction of the present invention. Indene oxide is too acid-sensitive to be prepared using mCPBA, but is easily prepared by the reaction of the present invention.

Substrates for the invention include among others unbranched olefins, branched olefins, cyclic olefins, exocyclic olefins, olefins with aromatic substituents. The following olefins, for example, can be epoxidized by the method of invention: styrene; methylene cyclohexane; trans-2,2-dimethyl-3-heptene; limonene; 1,3-cyclooctadiene; α-pinene, β-pinene, indene.

In the preferred embodiment, the substrate should be substantially soluble in a protic, simple alcohol solvent. The reaction of this invention is particularly useful for epoxidation of olefins that are soluble in protic solvent.

The method of invention can be performed with either mild acid or mild base. For these purposes, the term "mild," or equivalently "weak", refers to an acid or base which is substantially un-ionized. Strong refers to an acid or base which is substantially ionized. The base is inorganic, and examples include the following: sodium bicarbonate, potassium bicarbonate, disodium hydrogen phosphate, and trisodium phosphate. Strong organic bases, such as sodium methoxide or sodium ethoxide, should be avoided as they react with the product epoxide, thereby decreasing product yield. The acid should be mild, and examples include but are not limited to the following: mild acidic cation exchange resin. Triethyl aluminum, zinc bromide and boron trifluoride are not desirable acids because they lead to hydrolysis of carbodiimides and yield no epoxidation. Copper$^{(I)}$ chloride and cesium chloride also are not desirable acids because they catalyze the decomposition of hydrogen peroxide and yield no epoxidation. Aluminum chloride is not a desirable acid because it yields no epoxidation. In general, strong acids, such as toluene sulfonic acid, hydrochloric acid, or strongly acidic Amberlite resins, are not preferred for the present invention because they can protonate and thereby destroy the carbodiimide reagent. One of ordinary skill in the art can chose, in view of the guidance provided herein, appropriate mild acid or base conditions suitable for a particular solvent system, carbodiimide and starting reactant.

Although the reaction occurs using only 0.1 mole equivalent of base versus carbodiimide, the rate and yield of reaction are improved if stoichiometric amounts of base and carbodiimide are used. A slight excess of base and carbodiimide (relative to olefin) is preferred.

The choice of pressure, temperature and scale-up conditions are within the skill of the ordinary artisan and can be chosen routinely without undue experimentation. In the reaction of this invention the specific selections of acid or base, hydrogen peroxide concentration, solvent or solvent mixture, carbodiimide and reactant stoichiometry can be made without expense of undue experimentation by one of ordinary skill in the art in view of the description provided herein and what is well-known in the art.

In a specific embodiment of the invention, aqueous hydrogen peroxide is added to a mixture of substrate and carbodiimide in either basic or acidic protic, simple alcohol solvent. In the preferred embodiment, the hydrogen peroxide is aqueous and the solvent is a simple alcohol. The hydrogen peroxide can be between about 1% and 99% in aqueous solution. An ethereal anhydrous solution of hydrogen peroxide can also be used in the invention by adding such solution to the mixture of interest and then distilling off the ether. The reactants are preferably stirred for several hours, e.g., about two to about twenty four hours. Epoxide products are isolated and purified by standard methods. The progress of the reaction can be followed to near completion by standard methods, including thin-layer chromatography (TLC), infra-red spectroscopy (IR), nuclear magnetic resonance spectroscopy (NMR) and gas chromatography (GC). In the standard workup of the specific embodiment, solids (urea by-products and others) are removed by filtration. The filtrate is partitioned between ether and water. The ethereal phase is washed with brine, dried over $MgSO_4$ and concentrated. Product isolation is accomplished by chromatography on silica gel.

When the method is carried out on a large scale, e.g., about 10 grams or more of olefin substrate, adding the aqueous hydrogen peroxide slowly and cooling the reaction mixture are preferable because the reaction may be quite exothermic.

In some cases unreacted carbodiimide can co-elute with some epoxides on silica columns. All but the most acid-sensitive epoxides can be isolated from unreacted carbodiimide by stirring the crude ethereal extract with 5% aqueous acetic acid, and then washing with saturated aqueous sodium bicarbonate. Acid-sensitive epoxides are preferably isolated via distillation. Under acidic conditions, adding reagents, e.g., sodium bisulfite, to destroy excess hydrogen peroxide can lead to rapid decomposition of the epoxide.

Styrene was treated in methanol with a two-fold molar excess of DCC and a two-fold molar excess of $KHCO_3$ and a ten-fold excess of a 30% solution of hydrogen peroxide. After two hours at room temperature, the yield of styrene oxide was 75%. When the reaction was repeated using a weakly acidic cation exchange resin, Amberlite IRC-50, instead of the $KHCO_3$, the yield of styrene oxide after eight hours at room temperature was 73%. However, when this reaction was repeated without any carbodiimide under basic conditions ($KHCO_3$), the yield of styrene oxide was only 54% after 18 hours and under acidic conditions (exchange resin), the yield of styrene oxide was only 50–60% after about 18 hours. In comparison, the epoxidation of styrene using the Payne reaction (combining hydrogen peroxide with a nitrile) requires heating the reaction mixture to 50° C. for four hours, effecting a yield of 75%.

Undecylenic acid methyl ester was treated in methanol with a two-fold molar excess of DCC and a two-fold molar excess of $KHCO_3$ and a 10-fold excess of a 30% solution of hydrogen peroxide. After 24 hours at room temperature, the yield of epoxide was 64%. However, when this reaction was repeated without any carbodiimide, no epoxidation occurred.

In general, the yields obtained with the present invention are comparable to those obtained by the Payne oxidation (hydrogen peroxide and nitrile), and in some cases a little lower than those given by mCPBA. However, the fact that the present invention can be performed under either acidic or basic conditions affords a great advantage over the use of mCPBA oxidation.

Four specific embodiments A–D of this invention are based on variation of reaction conditions. (For these purposes, "excess" means more than one mole equivalent, wherein the reagent being compared to is present in only one mole equivalent.) (See Table 1 for definitions of conditions A–D.)

TABLE 1

Conditions A–D

| Embodiment/ Conditions | # of Equiv's of Olefin | # of Equiv's of Carbodiimide | Acid or Base, and # of Equiv's | Solvent | Hydrogen Peroxide | # of Hours Reaction Time |
|---|---|---|---|---|---|---|
| A | 1 | 2 | 2 equiv. base | methanol | >10 equiv., 30% | 14–24 |
| B | 5 | 1 | 1 equiv. base | ethanol | >10 equiv., 30% | 24–72 |
| C | 1 | 2 | acid | methanol | >10 equiv., 30% | 24 |
| D | 5 | 1 | acid | ethanol | >10 equiv., 30% | 24 |

A) 1 mole equivalent of substrate olefin; excess carbodiimide, e.g., 2 mole equivalents; excess base, e.g., 2 mole equivalents of potassium bicarbonate; excess hydrogen peroxide, e.g., 13 mole equivalents of (30%) hydrogen peroxide; 14–24 hours at room temperature.
B) Excess substrate olefin, e.g., 5 mole equivalents; one mole equivalent of carbodiimide; one equivalent of base, e.g., potassium bicarbonate; excess hydrogen peroxide, e.g., 13 mole equivalents of (30%) hydrogen peroxide; 24–72 hours at room temperature.
C) 1 mole equivalent of substrate olefin; excess carbodiimide, e.g., 2 mole equivalents; acid; excess hydrogen peroxide, e.g., 13 mole equivalents of (30%) hydrogen peroxide; 24 hours at room temperature.
D) Excess substrate olefin, e.g., 5 mole equivalents; one mole equivalent of carbodiimide; acid; excess hydrogen peroxide, e.g., 13 mole equivalents of (30%) hydrogen peroxide; 24 hours at room temperature.

Each of these sets of conditions can lead to epoxidation, but yields can be optimized by one of ordinary skill in the art in any given reaction for a given olefin by routine choice of solvent, carbodiimide, and acid or base.

All yields are calculated by the standard methods in chemical practice, i.e., actual yield divided by the theoretical yield defined by the limiting reagent, which is the carbodiimide in conditions B and D.

The reaction of this invention is illustrated by the specific reactions with conditions and results listed in Tables 2–7. (The first 15 reactions in each of Tables 2, 5, 6, and 7 are illustrated with chemical structures in the Examples.) For comparison, Tables 8 and 9 illustrate reactions using mCPBA and nitriles (Payne conditions), respectively.

TABLE 2

Reactions Using Conditions A[1]

| Solvent | Olefin Substrate | Base | Epoxide Yield, % |
|---|---|---|---|
| MeOH | methylenecyclohexane | $KHCO_3$ | 74 |
| EtOH | allylbenzene | $KHCO_3$ | 59 |
| iPrOH | 1-dodecene | $KHCO_3$ | 40 |
| MeOH | trans-2,2-dimethyl-3-heptene | $KHCO_3$ | 38 |
| MeOH | cyclohexene-4-carbinol acetate | $KHCO_3$ | 62[2] |

TABLE 2-continued

Reactions Using Conditions A[1]

| Solvent | Olefin Substrate | Base | Epoxide Yield, % |
|---|---|---|---|
| MeOH | styrene | $KHCO_3$ | 75 |
| MeOH | indene | $KHCO_3$ | 67 |
| MeOH | cyclohexene-1-carbinol | $KHCO_3$ | 65 |
| MeOH | 2-methylcyclohexene-1-carbinol | $KHCO_3$ | 67 |
| MeOH | 1-methyl-4-isopropylcyclohexene | $KHCO_3$ | 83[3] |
| MeOH | (+)-limonene | $KHCO_3$ | 35% + 10% (3 epoxide products)[4] |
| MeOH | 1,3-cyclooctadiene | $KHCO_3$ | 39% + 24% (2 epoxide products)[5] |
| MeOH | bicyclo[2.2.1]hept-2-ene | $KHCO_3$ | 64 |
| MeOH | (−)-β-pinene | $KHCO_3$ | 91 |
| MeOH | α-pinene | $KHCO_3$ | 68 |
| MeOH | α-pinene | $Na_2HPO_4$ | 54 |
| MeOH | α-pinene | $Na_3PO_4$ | 59 |
| MeOH | α-pinene | $KHCO_3$ | 68[6] |
| MeOH | α-pinene | $KHCO_3$ | 52[7] |
| EtOH | α-pinene | $KHCO_3$ | 28[8] |
| MeOH | α-pinene | NaOEt[9] | trace |
| MeOH | 2-cyclohexenone | $KHCO_3$ | >95[10] |
| MeOH/$H_2O$ 5/3 | α-pinene | $KHCO_3$ | 35[11] |
| MeOH | pyrene | $KHCO_3$ | 0 |
| MeOH | cyclohexanone[12] | $KHCO_3$ | 0 epoxide, 0 lactone |

[1]The base (2.0 molar equivalents relative to the olefin) was suspended in a solution of the olefin (100 mg) and the carbodiimide (2.0 molar equivalents relative to olefin) which was DCC unless otherwise noted, in 5 mL of solvent. Hydrogen peroxide (1 mL of 30% solution, 9.8 mmol) was added (except where noted) and the mixture was stirred at room temperature for 24 hrs.
[2]The 7-oxabicyclo[4.1.0]heptane-3-methanol acetate product was a 1:1 mixture of diastereomers.
[3]The 1-methyl-4-(1-methylethyl)-7-oxabicyclo[4.1.0]heptane was a 1:1 mixture of diastereomers.
[4]Chromatography of the products yielded two fractions. The first consisted of a 2:3 mixture (35%) of 1-methyl-4-(1-methylethenyl)-7-oxabicyclo[4.1.0]heptane and 2-methyl-2-(4-methyl-3-cyclohexen-1-yl)-oxirane. The second fraction consisted of 1-methyl-4-(2-methyloxiranyloxabicyclo[4.1.0]heptane (10%). No stereoselectivity was observed in any of these products.
[5]Chromatography of the products yielded two products: 9-oxabicyclo[6.1.0]non-2-ene (39%) and 3,10-dioxatricyclo[7.1.0.0$^{2,4}$]decane (24%).
[6]DIC was the carbodiimide used.
[7]EDC was the carbodiimide used.
[8]Anhydrous $H_2O_2$ in ethanol (5 mL, 2.5 M) was used instead of aqueous $H_2O_2$.
[9]NaOEt (0.14 molar equiv relative to olefin) was used instead of $KHCO_3$ or $NaHCO_3$.
[10]After 20 min of reaction, TLC and $^1H$ NMR indicated complete conversion of the enone to the corresponding epoxide, but no conversion of DCC to DCU.
[11]Water (3 mL) was added to the normal 5 mL of methanol to make the solvent system. Two liquid phases were evident in the reaction mixture.
[12]Cyclohexanone was used instead of any olefin substrate to determine whether (undesired) Baeyer-Villiger oxidation of a carbonyl functionality would occur. After 48 hr. $^1H$ NMR detected unreacted cyclohexanone but no Baeyer-Villiger product (lactone).

The data in Table 2 illustrate the reaction of this invention in the specific embodiment in which conditions A are used. Diastereomeric mixtures of products are formed from epoxidation of cyclohexene-4-carbinol acetate and 1-methyl-4-isopropylcyclohexene. Epoxidation of (+)-limonene yielded two mono-epoxide products and the bis-epoxide. Epoxidation of 1,3-cyclooctadiene yielded both the mono-epoxide and the bis-epoxide.

Mild bases besides $KHCO_3$ are acceptable, as the experiments with $Na_2HPO_4$ and $Na_3PO_4$ illustrate. Carbodiimides besides DCC are acceptable, as the experiments with DIC and EDC illustrate. The hydrogen peroxide need not be aqueous, as the experiment with anhydrous hydrogen peroxide in ethanol solvent shows. The use of a strong base, e.g., sodium ethoxide, may lead to lower yields, probably because of reaction of the product epoxide with the strong base.

Enones are not good substrates for this reaction, as mentioned above. The enone 2-cyclohexenone is epoxidized under the conditions used in Table 2; however, the reaction does not involve the carbodiimide as evidenced by the recovery of the unreacted carbodiimide. A control experiment in which 2-cyclohexenone was reacted under the conditions A in Table 2 except that no carbodiimide was included yielded complete conversion to the product epoxide. As mentioned above, enones undergo a Michael-type addition reaction with hydroperoxide anion to form the epoxide.

The experiment with pyrene illustrates that fused aromatics are not good substrates for the reaction of this invention, probably because of their poor solubility in protic, simple alcohol solvent and because of the unfavorable thermodynamics of destroying aromaticity via epoxidation. The experiment with cyclohexanone illustrates that the reaction conditions of this invention do not lead to undesired Baeyer-Villiger oxidation.

TABLE 3

Reactions with Excess Base and Various Solvents[1]

| Solvent | Olefin Substrate | Base | Epoxide Yield, % |
|---|---|---|---|
| acetone | α-pinene | NaHCO$_3$ | trace |
| 1,4-dioxane | α-pinene | NaHCO$_3$ | trace |
| DMF | α-pinene | NaHCO$_3$ | trace |
| EtOH/ethyl acetate, 3/2 | pyrene | KHCO$_3$ | 0 |
| MeOH/ethyl acetate, 1/1 | pyrene | KHCO$_3$ | trace[2] |
| dry ether | β-pinene | KHCO$_3$ | 0[3] |
| benzyl alcohol | α-pinene | KHCO$_3$ | 0 |
| benzyl alcohol/MeOH, 1/1 | α-pinene | KHCO$_3$ | 38 |
| MeOH | α-pinene | KHCO$_3$ | 0[4] |
| H$_2$O | oleic acid | KHCO$_3$ | 0[5] |
| phenol/MeOH 1/1 | α-pinene | KHCO$_3$ | 20[6] |
| (Et)$_3$NH | α-pinene | KHCO$_3$ | 0 |

[1]These experiments were conducted in 5 mL of solvent with 2 molar equivalents of base and 2 molar equivalents of DCC (relative to olefin substrate, 100 mg) and hydrogen peroxide (1 mL of 30% solution, 9.8 mmol, except where noted otherwise). The effect of solvent choice is illustrated.
[2]The mixture was stirred for 3 days during which TLC indicated gradual production of a more polar compound. $^1$H NMR detected unreacted pyrene and trace pyrene 4,5-pyrene oxide.
[3]The solvent was dry (anhydrous) ether at 0° C. Anhydrous hydrogen peroxide (5.24 mL, 7.34 mmol of 1.4 M in ether) was added. The mixture was allowed to warm to room temp. and stirred for 24 hr.
[4]t-Butyl hydroperoxide (1.34 mL, 9.8 mmol of 70% aqueous solution) and water (0.75 mL) were used instead of aqueous hydrogen peroxide.
[5]An extra molar equivalent of base was used to deprotonate the oleic acid, thus a total of 3 molar equivalents of KHCO$_3$ were used.
[6]The yield of crude product was greater than 50%. Isolation of the product from phenol/MeOH yielded only about 20% product.

The conditions of the experiments in Table 3 are similar to conditions A, but differ in most cases in the solvent. The experiments in acetone, 1,4-dioxane, and DMF illustrate that aprotic solvents are not preferred. Pyrene, a fused aromatic compound, yielded no epoxidation in a solvent system of ethanol and ethyl acetate, but it yielded a trace amount of epoxidation in a solvent system of methanol and ethyl acetate. When dry ether was the solvent and anhydrous hydrogen peroxide was used, β-pinene was not epoxidized, illustrating the need for some protic component of the reaction mixture (to stabilize either the transition state or the peroxyisourea intermediate via hydrogen-bonding). Compare this to the reaction in Table 2 of α-pinene with anhydrous hydrogen peroxide in ethanol which yielded 28% epoxide; in this case, the proticity of the ethanol solvent was sufficient, despite the lack of water in the hydrogen peroxide, to stabilize the transition state or intermediate. The experiments with benzyl alcohol indicate that simple alkyl alcohol solvent systems are preferred. The experiment with t-butyl hydroperoxide which yielded no epoxidation illustrates that hydrogen peroxide is required for the reaction of this invention and supports the proposed mechanism for the reaction set forth above. The experiment with oleic acid in water yielded no epoxidation presumably because the oleic acid substrate was not dissolved; probably only an emulsion was present which didn't allow for epoxidation. The experiment in triethylamine solvent shows that amines are not useful solvents for the reaction of this invention.

TABLE 4

Reaction of α-pinene under Conditions A except that hydrogen peroxide concentrations are varied[1]

| # of mmoles of H$_2$O$_2$ | # of molar equivalents of H$_2$O$_2$ (relative to olefin) | Epoxide yield, % |
|---|---|---|
| 9.8 | 13.4 | 68 |
| 4.9 | 6.7 | 51 |
| 2.45 | 3.3 | 58 |
| 1.23 | 1.7 | 57 |
| 0.81 | 1.1 | 27 |

[1]KHCO$_3$ (2.0 molar equivalents relative to olefin) was suspended in a solution of α-pinene (100 mg) and DCC (2.0 molar equivalents relative to olefin) in 5 mL of methanol. Diluted hydrogen peroxide (1 mL) was used. Hydrogen peroxide was diluted in various amounts to determine the effect of H$_2$O$_2$ stoichiometry on product yield.

The data in Table 4 indicate that it is preferable to have at least a slight excess of hydrogen peroxide (relative to olefin). Epoxide yields are improved when at least a slight excess of hydrogen peroxide (relative to olefin) is used.

TABLE 5

Reactions Using Conditions B[1]

| Solvent | Olefin Substrate | Base | Epoxide Yield, % |
|---|---|---|---|
| EtOH | methylenecyclohexane | KHCO$_3$ | 89% |
| EtOH | allylbenzene | KHCO$_3$ | 61 |
| EtOH | 1-dodecene | KHCO$_3$ | 28 |
| EtOH | trans-2,2-dimethyl-3-heptene | KHCO$_3$ | 36 |
| EtOH | cyclohexene-4-carbinol acetate | KHCO$_3$ | 68[2] |
| EtOH | styrene | KHCO$_3$ | 80 |
| EtOH | indene | KHCO$_3$ | 59 |
| EtOH | cyclohexene-1-carbinol | KHCO$_3$ | 68 |
| EtOH | 2-methylcyclohexene-1-carbinol | KHCO$_3$ | 70 |
| EtOH | 1-methyl-4-isopropylcyclohexene | KHCO$_3$ | 61[3] |
| EtOH | (+)-limonene | KHCO$_3$ | 85% + 2% (3 epoxide products) [4] |
| EtOH | 1,3-cyclooctadiene | KHCO$_3$ | 65[5] |
| EtOH | bicyclo[2.2.1]hept-2-ene | KHCO$_3$ | 61 |
| EtOH | (−)-β-pinene | KHCO$_3$ | 60 |
| EtOH | α-pinene | KHCO$_3$ | 83 |
| EtOH | (−)-β-pinene | KHCO$_3$ | 60[6] |
| EtOH | α-pinene | KHCO$_3$ | 14[7] |

TABLE 5-continued

Reactions Using Conditions B[1]

| Solvent | Olefin Substrate | Base | Epoxide Yield, % |
|---|---|---|---|
| MeOH/ethyl acetate 1/1 | α-pinene | KHCO$_3$ | 71[8] |
| MeOH/ethyl acetate 1/1 | α-pinene | Na$_3$PO$_4$ | 83 |
| THF/water 3/1 | α-pinene | KHCO$_3$ | trace[9] |

[1]Except where otherwise noted, the base (1.0 molar equivalents relative to carbodiimide) was suspended in a solution of the olefin (5 molar equivalents relative to carbodiimide) and DCC (1.0 molar equivalents relative to base) in 5 mL of solvent. Hydrogen peroxide (1 mL of 30% solution, 9.8 mmol) was added and the mixture was stirred at room temperature for 24 hrs.
[2]The product 7-oxabicyclo[4.1.0]heptane-3-methanol acetate was a 1:1 mixture of diastereomers.
[3]The 1-methyl-4-(1-methylethyl)-7-oxabicyclo[4.1.0]heptane was a 1:1 mixture of diastereomers.
[4]Chromatography of the products yielded two fractions. The first consisted of a 2:3 mixture (85%) of 1-methyl-4-(1-methylethenyl)-7-oxabicyclo[4.1.0]heptane and 2-methyl-2-(4-methyl-3-cyclohexen-1-yl)-oxirane. The second fraction consisted of 1-methyl-4-(2-methyloxiranyl)oxabicyclo[4.1.0]heptane (2%). No stereoselectivity was observed in any of these products.
[5]Only the monoepoxide, 9-oxabicyclo[6.1.0]non-2-ene, formed.
[6]This reaction was done on a large scale, and the conditions varied from those of B in the following ways. KHCO$_3$ (2.0 molar equivalents relative to DCC) was suspended in a solution of (−)-β-pinene (66.1g, 485 mmol, 5 molar equivalents relative to DCC) in 300 mL of ethanol. H$_2$O$_2$ (100 mL of 30% solution, 980 mmol) was added dropwise over 6 hr. A water bath was used to keep the temperature below 25° C. The mixture was stirred at RT for an additional 18 hr.
[7]The mixture was heated to 55° C. over 5 hr., after which TLC indicated most of the DCC had been converted to DCU.
[8]After the mixture had been stirred for 24 hr. at room temp., TLC indicated most of the substrate and DCC were unchanged. The mixture was heated to reflux, and after 3 hr. DCC was not detected and the yield of the product epoxide was 71%.
[9]The reaction was stirred for 4 days.

The data in Table 5 illustrate the reaction of this invention in the specific embodiment in which conditions B are used. Diastereomeric mixtures of products were formed from epoxidation of cyclohexene-4-carbinol acetate and 1-methyl-4-isopropylcyclohexene. Epoxidation of (+)-limonene yielded two mono-epoxide products and the bis-epoxide. Unlike under conditions A, epoxidation of 1,3-cyclooctadiene under conditions B yielded only the mono-epoxide.

The reaction of α-pinene in ethanol at room temperature yielded 83% epoxide, but when the same reaction was performed at 55° C. for 5 hr., the yield was only 14%, illustrating that heating the reaction is not preferred probably because this leads to product epoxide decomposition. The reaction of α-pinene in a mixture of THF and water yielded only trace epoxidation, indicating that addition of aprotic solvent may lead to decreased product yield. Similarly, the reaction of α-pinene in a mixture of methanol and ethyl acetate yielded only trace epoxide formation after 24 hr. at room temperature, indicating that addition of aprotic solvent may make the reaction sluggish and decrease product yield. However, when this same reaction mixture was subsequently heated to reflux for 3 hr., the product yield was 71%. In this experiment it appears that heating the reaction helped to compensate for the addition of an aprotic solvent. In all other experiments, heat has led to decreased product yields, presumably because heat promotes nucleophilic addition of the solvent to the product epoxide, thereby destroying the product. The reaction of α-pinene in a mixture of methanol and ethyl acetate with a base stronger than KHCO$_3$, i.e., Na$_3$PO$_4$, yielded 83% epoxide; this indicates that when an aprotic solvent is part of the solvent system, the effect of its presence on product yield can be counteracted to some extent by using a stronger base.

TABLE 6

Reactions Using Conditions C[1]

| Solvent | Olefin Substrate | Acid | Epoxide Yield, % |
|---|---|---|---|
| MeOH | methylenecyclohexane | Amberlite IRC-50 | 70 |
| MeOH | allylbenzene | Amberlite IRC-50 | 42 |
| MeOH | 1-dodecene | Amberlite IRC-50 | 27 |
| MeOH | trans-2,2-dimethyl-3-heptene | Amberlite IRC-50 | 14 |
| MeOH | cyclohexene-4-carbinol acetate | Amberlite IRC-50 | 29[2] |
| MeOH | styrene | Amberlite IRC-50 | 73[3] |
| MeOH | indene | Amberlite IRC-50 | 73 |
| MeOH | cyclohexene-1-carbinol | Amberlite IRC-50 | 57 |
| MeOH | 2-methylcyclohexene-1-carbinol | Amberlite IRC-50 | 63 |
| MeOH | 1-methyl-4-isopropylcyclohexene | Amberlite IRC-50 | 38[4] |
| MeOH | (+)-limonene | Amberlite IRC-50 | 49% + 15% (3 epoxide products)[5] |
| MeOH | 1,3-cyclooctadiene | Amberlite IRC-50 | 18% + 17% (2 epoxide products)[6] |
| MeOH | bicyclo[2.2.1]hept-2-ene | Amberlite IRC-50 | 68 |
| MeOH | (−)-β-pinene | Amberlite IRC-50 | 48 |
| MeOH | α-pinene | Amberlite IRC-50 | 73 |
| MeOH | undecylenic acid methyl ester | Amberlite IRC-50 | 66 |
| MeOH | 1-dodecene | toluenesulfonic acid[7] | 15 |
| MeOH | 1-dodecene | hydrochloric acid[8] | 7 |
| MeOH | 1-dodecene | Amberlite IR-120[9] | 16 |

[1]Except where noted otherwise, Amberlite IRC-50 (10 mg) was suspended in a solution of the olefin (100 mg) and DCC (2.0 molar equivalents relative to the olefin) in 5 mL of methanol. Hydrogen peroxide (1 mL of 30% solution, 9.8 mmol) was added and the mixture was stirred at room temperature for 24 hr.
[2]The product 7-oxabicyclo[4.1.0]heptane-3-methanol acetate was a 1:1 mixture of diastereomers.

TABLE 6-continued

Reactions Using Conditions C[1]

| Solvent | Olefin Substrate | Acid | Epoxide Yield, % |
|---|---|---|---|

[3]TLC indicated conversion was complete after 8 hrs.
[4]The 1-methyl-4-(1-methylethyl)-7-oxabicyclo[4.1.0]heptane was a 1:1 mixture of diastereomers.
[5]Chromatography of the products yielded two fractions. The first consisted of a 2:3 mixture (49%) of 1-methyl-4-(1-methylethenyl)-7-oxabicyclo[4.1.0]heptane and 2-methyl-2-(4-methyl-3-cyclohexen-1-yl)-oxirane. The second fraction consisted of 1-methyl-4-(2-methyloxiranyloxabicyclo[4.1.0]heptane (15%). No stereoselectivity was observed in any of these products.
[6]Chromatography of the products yielded two products: 9-oxabicyclo[6.1.0]non-2-ene (18%) and 3,10-dioxatricyclo[7.1.0.0$^{2,4}$]decane (17%).
[7]Toluenesulfonic acid hydrate (6 mg, 0.06 mmol) was used instead of the amberlite beads.
[8]Hydrochloric acid (250 μL of 0.12 M solution in methanol, 0.030 mmol) was used instead of the amberlite beads.
[9]Amberlite IR-120 beads were used instead of the Amberlite IRC-50 beads.

The experiments in Table 6 illustrate the reaction of this invention in the specific embodiment in which conditions C are used. As under conditions A and B, diastereomeric mixtures of products were formed from epoxidation of cyclohexene-4-carbinol acetate and 1-methyl-4-isopropylcyclohexene. Also as under conditions A and B, epoxidation of (+)-limonene yielded two mono-epoxide products and the bis-epoxide. As under conditions A, epoxidation of 1,3-cyclooctadiene under conditions C yielded both the mono-epoxide and the bis-epoxide. The three experiments in which acids stronger than Amberlite IRC-50 were used, i.e., those with toluenesulfonic acid, hydrochloric acid, and Amberlite IR-120, product yields were substantially decreased.

Using 100 mg of the Amberlite 1RC-50 beads, instead of 10 mg, did not affect epoxidation yields (data not shown). Cyclohexenone was not epoxidized under conditions C in the presence or absence of DCC, further indicating that enones are not useful substrates for the reaction of this invention (data not shown).

TABLE 7

Reactions Using Conditions D[1]

| Solvent | Olefin Substrate | Acid | Epoxide Yield, % |
|---|---|---|---|
| EtOH | methylenecyclohexane | Amberlite IRC-50 | 72 |
| EtOH | allylbenzene | Amberlite IRC-50 | 45 |
| EtOH | 1-dodecene | Amberlite IRC-50 | 32 |
| EtOH | trans-2,2-dimethyl-3-heptene | Amberlite IRC-50 | 19 |
| EtOH | cyclohexene-4-carbinol acetate | Amberlite IRC-50 | 62[2] |
| EtOH | styrene | Amberlite IRC-50 | 39 |
| EtOH | indene | Amberlite IRC-50 | 98 |
| EtOH | cyclohexene-1-carbinol | Amberlite IRC-50 | 60 |
| EtOH | 2-methylcyclohexene-1-carbinol | Amberlite IRC-50 | 65 |
| EtOH | 1-methyl-4-isopropylcyclohexene | Amberlite IRC-50 | 44[3] |
| EtOH | (+)-limonene | Amberlite IRC-50 | 75% + 1% (3 epoxide products)[4] |
| EtOH | 1,3-cyclooctadiene | Amberlite IRC-50 | 12[5] |
| EtOH | bicyclo[2.2.1]hept-2-ene | Amberlite IRC-50 | 57 |
| EtOH | (−)-β-pinene | Amberlite IRC-50 | 65 |
| EtOH | α-pinene | Amberlite IRC-50 | 68 |

[1]Except where noted otherwise, Amberlite IRC-50 (10 mg) was suspended in a solution of the olefin (5.0 molar equivalents relative to DCC) and DCC (150 mg, 0.727 mmol) in 5 mL of ethanol. Hydrogen peroxide (1 mL of 30% solution, 9.8 mmol) was added and the mixture was stirred at room temperature for 24 hr.
[2]The product 7-oxabicyclo[4.1.0]heptane-3-methanol acetate was a 1:1 mixture of diastereomers.
[3]The 1-methyl-4-(1-methylethyl)-7-oxabicyclo[4.1.0]heptane was a 1:1 mixture of diastereomers.
[4]Chromatography of the products yielded two fractions. The first consisted of a 2:3 mixture (75%) of 1-methyl-4-(1-methylethenyl)-7-oxabicyclo[4.1.0]heptane and 2-methyl-2-(4-methyl-3-cyclohexen-1-yl)-oxirane. The second fraction consisted of 1-methyl-4-(2-methyloxiranyloxabicyclo[4.1.0]heptane (1%). No stereoselectivity was observed in any of these products.
[5]Only the monoepoxide, 9-oxabicyclo[6.1.0]non-2-ene, formed.

The experiments in Table 7 illustrate the reaction of this invention in the specific embodiment in which conditions D are used. Diastereomeric mixtures of products were formed from epoxidation of cyclohexene-4-carbinol acetate and 1-methyl-4-isopropylcyclohexene. Epoxidation of (+)-limonene yielded two mono-epoxide products and the bis-epoxide. As under conditions B, epoxidation of 1,3-cyclooctadiene under conditions D yielded only the mono-epoxide.

The data in Tables 2–7 illustrate the reaction of this invention. The choice of reaction conditions should depend on relative cost and abundance of olefin and/or carbodiimide. The use of excess carbodiimide may require longer reaction times. When the carbodiimide is the limiting reagent (and the olefin is in excess, conditions B and D), ethanol is the preferred solvent because it prevents phase separation.

Epoxidation reactions with certain olefins are stereoselective in the reaction of this invention. Facial selectivity was observed with rigid bicyclic compounds. See Examples 15 (bicyclo[2.2.1]hept-2-ene), 16 ((−)-β-pinene), and 17 (α-pinene) below. Similar facial selectivity is seen also in some compounds with a hydroxyl group separated from the double bond by 1 to 4 carbons. This is known to those skilled in the art as the Henbest directing effect. (Henbest, H. B.; Wilson, R. A. L. *J. Chem. Soc.* 1957, 1958.) The Henbest directing effect refers to the stereoselective formation of epoxides from cyclic alcohols on the side cis to the hydroxyl group. Some substrates with a hydroxyl group separated from the double bond by 1, 2, or 3 carbons can be oxidized stereoselectively. See Example 19.

In other methods of epoxidizing olefins, the relative rate of epoxidation increases with the number of alkyl substituents. (March *Advanced Organic Chemistry*, 4th ed. Wiley, NY, 1992, p. 826). And this difference in reactivity permits the selective oxidation of the more substituted double bond in nonconjugated diolefins. For instance, using mCPBA to epoxidize (+)-limonene yields epoxidation only at the trisubstituted double bond. However, using Payne conditions to epoxidize (+)-limonene yields a 1:1 mixture of monoepoxides; the di-substituted and tri-substituted double bonds are equally likely to be epoxidized. The reaction of this invention yields a 3:2 mixture of mono-epoxides, being somewhat selective for the tri-substituted double bond. Carbodiimide epoxidation also gives a small amount of the bis-epoxide.

If the substrate contains a conjugated diene, and excess carbodiimide is used, bis-epoxidation occurs. But when excess substrate is used, the mono-epoxide is formed exclusively. See Example 14 (1,3-cyclooctadiene) below.

The reactions of this invention can yield epoxide intermediates which can be used in combination with other reactions and methods known to those of ordinary skill in the art to produce other products.

The yields of the reaction of this invention are, in general, comparable to yields accomplished by the Payne reaction but in some cases lower than those using high quality mCPBA. It is known to those skilled in the art, however, that mCPBA is becoming less commercially available and more expensive because of hazards in its production. Data from experiments using mCPBA and the Payne conditions are given below in Tables 8 and 9, respectively, to be compared to data from the reaction of this invention in Tables 2–7.

TABLE 8

Comparative Data Using mCPBA[1]

| Olefin Substrate | Epoxide Yield, % |
|---|---|
| methylenecyclohexane | 75 |
| allylbenzene | 84 |
| 1-dodecene | 91 |
| trans-2,2-dimethyl-3-heptene | 59 |
| cyclohexen-4-carbinol acetate | 75[2] |
| styrene | 88 |
| indene | 0[3] |
| cyclohexene-1-carbinol | 68 |
| 2-methylcyclohexen-1-carbinol | 70 |
| 1-methyl-4-isopropylcyclohexene | 73[4] |
| (+)-limonene | 75% + 11% (2 epoxide products)[5] |
| 1,3-cyclooctadiene | 80[6] |
| bicyclo[2.2.1]hept-2-ene | 79 |

TABLE 8-continued

Comparative Data Using mCPBA[1]

| Olefin Substrate | Epoxide Yield, % |
|---|---|
| (−)-β-pinene | 0[7] |
| α-pinene | 74 |

[1]To a 0° C. solution of 100 mg of the olefin in dichloromethane was added a solution of mCPBA (1.3 molar equivalents relative to the olefin) in dichloroemethane. The mixture was warmed to room temperature while stirring overnight, then washed with saturated aqueous NaHCO$_3$ followed by brine, dried over MgSO$_4$ and concentrated.
[2]The product 7-oxabicyclo[4.1.0]heptane-3-methanol acetate was a 1:1 mixture of diastereomers.
[3]The reaction was monitored by TLC, which after 2 hr. indicated complete conversion of the substrate to a complex mixture. After standard workup, none of the intended epoxide was evident by $^1$H NMR analysis on the crude mixture.
[4]The 1-methyl-4-(1-methylethyl)-7-oxabicyclo[4.1.0]heptane was a 1:1 mixture of diastereomers.
[5]Chromatography of the products yielded two fractions. The first consisted of (75%) of 1-methyl-4-(1-methylethenyl)-7-oxabicyclo[4.1.0]heptane and a trace of 2-methyl-2-(4-methyl-3-cyclohexen-1-yl)-oxirane. The second fraction consisted of 1-methyl-4-(2-methyloxiranyloxabicyclo[4.1.0]heptane (11%). No stereoselectivity was observed in any of these products.
[6]Reaction progress was monitored by TLC analysis, which after 30 min indicated complete conversion of the substrate to a single product.
[7]Reaction progress was monitored by TLC analysis, which indicated complete conversion of the substrate to a complex mixture. After standard workup, none of the intended epoxide was evident by $^1$H NMR analysis.

TABLE 9

Comparative Date Using Payne Conditions[1]

| Substrate Olefin | Epoxide Yield, % |
|---|---|
| methylenecyclohexane | 47 |
| allylbenzene | 41 |
| 1-dodecene | 36[2] |
| trans-2,2-dimethyl-3-heptene | 15 |
| cyclohexene-4-carbinol acetate | 52[3] |
| styrene | 68 |
| indene | 42 |
| cyclohexene-1-carbinol | 67 |
| 2-methylcyclohexene-1-carbinol | 64 |
| 1-methyl-4-isopropylcyclohexene | 63[4] |
| (+)-limonene | 70% + 16% (3 epoxide products)[5] |
| 1,3-cyclooctadiene | 46% + 13% (2 epoxide products)[6] |
| bicyclo[2.2.1]hept-2-ene | 48 |
| (−)-β-pinene | 27 |
| α-pinene | 33 |

[1]Solid KHCO$_3$ (1.0 molar equivalent relative to the olefin) is suspended in a solution of the olefin (100 mg), and benzonitrile (1.5 molar equivalents relative to the olefin) in 1 mL of methanol (except where noted otherwise). Hydrogen peroxide (30% solution, 1.5 molar equivalents relative to olefin) is added and the mixture is stirred at room temperature for 48 hr.
[2]Isopropenol was the solvent.
[3]The product 7-oxabicyclo[4.1.0]heptane-3-methanol acetate was a 1:1 mixture of diastereomers.
[4]The 1-methyl-4-(1-methylethyl)-7-oxabicyclo[4.1.0]heptane was a 1:1 mixture of diastereomers.
[5]Chromatography of the products yielded two fractions. The first consisted of a 1:1 mixture (70%) of 1-methyl-4-(1-methylethenyl)-7-oxabicyclo[4.1.0] heptane and 2-methyl-2-(4-methyl-3-cyclohexen-1-yl)-oxirane. The second fraction consisted of 1-methyl-4-(2-methyloxiranyloxabicyclo[4.1.0]heptane (16%). No stereoselectivity was observed in any of these products.
[6]Chromatography of the products yielded two products: 9-oxabicyclo[6.1.0] non-2-ene (46%) and 3,10-dioxatricyclo[7.1.0.0$^{2,4}$]decane (13%).

By comparing the data from the reaction of this invention (Tables 2–7) to the data from other methods for epoxidizing olefins (Tables 8 and 9), it is evident that the reaction of this invention offers yields comparable to those offered by the Payne method and only slightly less than those offered by the method using mCPBA. Given the convenience and safety of the reaction of this invention, it is preferable to other methods.

The following examples illustrate the invention, but are in no way intended to limit the invention. All references cited in this specification are incorporated in their entirety by reference herein.

EXAMPLES

Example 1

Solid potassium bicarbonate (147 mg, 1147 mmol) was suspended in a solution of (−)-β-pinene (100 mg, 0.73 mmol), and dicyclohexylcarbodiimide (303 mg, 1.47 mmol) in methanol (5 mL). Hydrogen peroxide (1 mL of 30% solution, 9.8 mmol) was added, and the mixture was stirred at room temperature for twenty-four hours. Solids (urea by-product) were removed by filtration, and the filtrate was partitioned in a separatory funnel between ether (30 mL) and water (20 mL). The ethereal phase was washed with brine, dried over anhydrous magnesium sulfate, filtered and concentrated. The residue was chromatographed on silica gel, using hexanes:ether, 10:1, to isolate the epoxide (−)-β-pinene oxide (102 mg, 91%).

Repetition of this experiment using N,N'-diisopropylcarbodiimide or 1-ethyl-3-(3-dimethylaminopropyl)carbodiimide yielded (−)-β-pinene oxide in >70% yield. When 1-ethyl-3-(3-dimethylaminopropyl)carbodiimide was used, an extra equivalent of base was added to replace that consumed by the ammonium salt. On workup a saturated ammonium chloride wash facilitated the removal of the urea by-product.

Example 2

To a mixture of indene (426 mg, 3.67 mmol), dicyclohexylcarbodiimide (150 mg, 0.73 mmol), hydrogen peroxide (1 mL of 30% aqueous, 9.8 mmol) and ethanol (5 mL) was added 10 mg of cation exchange resin (mild) beads. The reaction mixture was stirred at room temperature for twenty-four hours. Filtration removed the dicyclohexylurea and the resin beads. The filtrate was partitioned in a separatory funnel between ether (30 mL) and water (20 mL). Standard ethereal workup, followed by column chromatography on silica gel (elution with hexanes:ether, 10:1) afforded indene epoxide (94 mg, 98%).

For Examples 3–17, the following conditions were used:

A) 1 equiv. of olefin; 2 equiv. of DCC; 2 equiv. of $KHCO_3$; 10–13 equiv. of 30% $H_2O_2$; methanol solvent; 14–24 hours at room temperature.

B) 5 equiv. of olefin; 1 equiv. of DCC; 1 equiv. of $KHCO_3$; 10–13 equiv. of 30% $H_2O_2$; ethanol solvent; 24–72 hours at room temperature.

C) 1 equiv. of olefin; 2 equiv. of DCC; cat. Amberlite resin; 10–13 equiv. of 30% $H_2O_2$; methanol solvent; 24 hours at room temperature.

D) 5 equiv. of olefin; 1 equiv. of DCC; cat. Amberlite resin; 10–13 equiv. of 30% $H_2O_2$; ethanol solvent; 24 hours at room temperature.

Example 3 styrene → styrene oxide
a) 75%
b) 80%
c) 73%
d) 39%
(75%)

Example 4 methylenecyclohexane → 1-methylcyclohexene oxide
a) 74%
b) 89%
c) 70%
d) 72%

Example 5 allylbenzene → allylbenzene epoxide
a) 59%
b) 61%
c) 42%
d) 45%

Example 6

$(CH_2)_9$—$CH_3$ → $(CH_2)_9$—$CH_3$ epoxide
a) 40%
b) 28%
c) 27%
d) 32%

Example 7 t-Bu—CH=CH—$C_3H_7$ → t-Bu—epoxide—$C_3H_7$
a) 48%
b) 36%
c) 14%
d) 19%

Example 8

OAc-cyclohexenyl → OAc-epoxycyclohexyl
a) 62%
b) 68%
c) 29%
d) 62%

Example 9 indene → indene oxide
a) 69%
b) 59%
c) 73%
d) 98%

Example 10

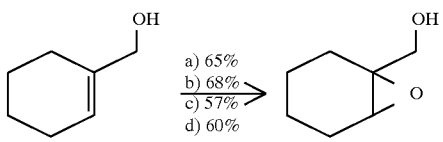

Example 11

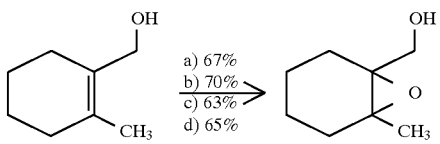

Example 12

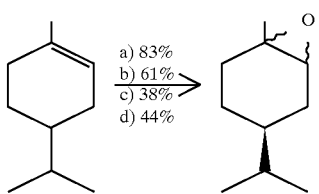

Example 13[(1)]

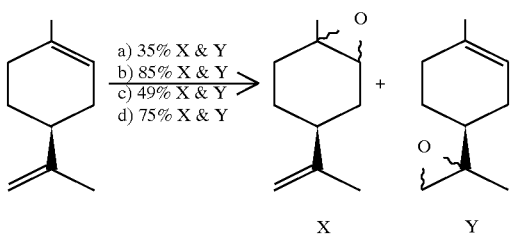

[(1)]In all cases, small amounts of the bis-epoxide were made.

Example 14

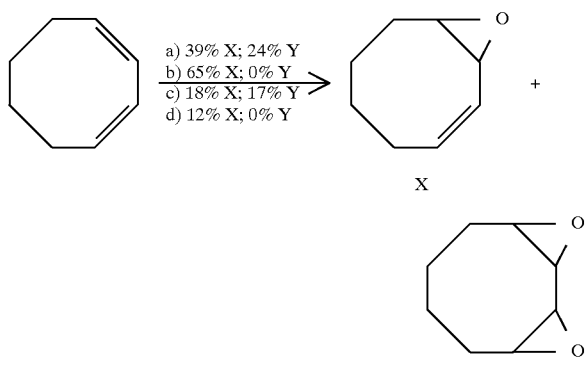

Example 15

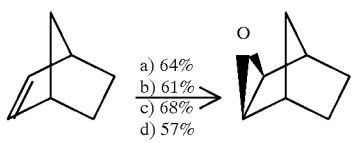

Example 16

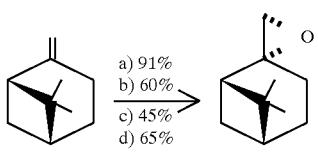

Example 17

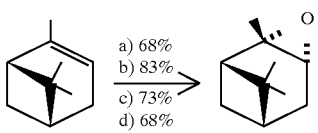

Example 18[(2)]

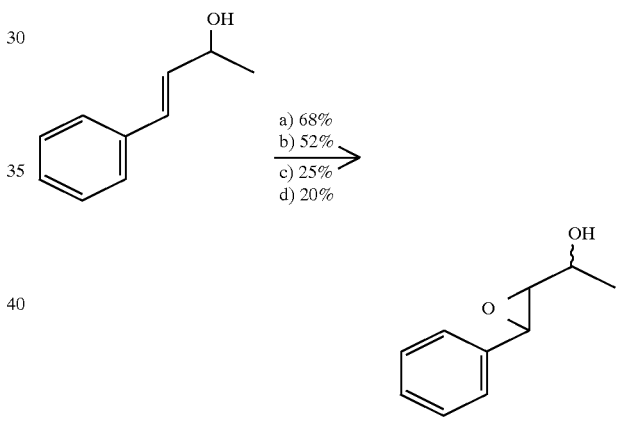

[(2)]A 1:3 mixture of diastereomers as measured by NMR. The absolute configuration of the individual products has not been determined.

Example 19[(3)]

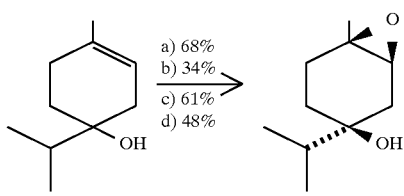

[(3)]Sole stereoisomer under all preferred embodiments of the present invention. See P. Garside and T. G. Hall, J. Chem Soc., (1969) p 716 for product structure.

What is claimed is:
1. A method for transferring an oxygen atom to an olefin comprising the step of: combining an olefin, hydrogen peroxide, a carbodiimide, and a reagent selected from the group of mild acid or mild base in a protic solvent system.

2. A method according to claim 1, wherein said carbodiimide is dicyclohexylcarbodiimide, N,N'-diisopropylcarbodiimide, or 1-ethyl-3-(3-dimethylaminopropyl)carbodiimide.

3. A method according to claim 1, wherein said protic solvent system comprises methanol, ethanol, n-propanol or isopropyl alcohol.

4. A method according to claim 1, wherein said hydrogen peroxide is aqueous, containing about 1% to 99% water by volume.

5. A method according to claim 1, wherein said hydrogen peroxide is aqueous, containing about 2% to 97% water by volume.

6. A method according to claim 1, wherein said hydrogen peroxide is aqueous, containing about 50% to 90% water by volume.

7. A method according to claim 1, wherein said reagent is mild acid.

8. A method according to claim 1, wherein one mole equivalent of olefin substrate is reacted with more than one mole equivalent of carbodiimide; more than one mole equivalent of hydrogen peroxide; and mild acid.

9. A method according to claim 8, wherein the solvent system is methanol.

10. A method according to claim 1, wherein one mole equivalent of carbodiimide is reacted with more than one mole equivalent of olefin substrate; more than one mole equivalent of hydrogen peroxide; and mild acid.

11. A method according to claim 10, wherein the solvent system is ethanol.

12. A method according to claim 1 further comprising the step of heating said combination.

13. A method according to claim 1, wherein the product of the reaction is an epoxide.

14. A method for transferring an oxygen atom to an olefin comprising the step of:

combining an olefin, hydrogen peroxide, a carbodiimide, and a mild cationic exchange resin in a protic solvent system.

15. A method for transferring an oxygen atom to an olefin which is not a fused aromatic olefin comprising the step of: combining an olefin, hydrogen peroxide, a carbodiimide, and a reagent selected from the group of mild acid or mild base in a protic solvent system.

16. The method of claim 15 wherein said protic solvent system is a substantially protic solvent system.

17. A method for transferring an oxygen atom to an olefin comprising the step of:

combining an olefin, hydrogen peroxide, a carbodiimide, and a mild base in a protic solvent system.

18. A method according to claim 17, wherein said carbodiimide is dicyclohexylcarbodiimide, N,N'-diisopropylcarbodiimide, or 1-ethyl-3-(3-dimethylaminopropyl)carbodiimide.

19. A method according to claim 17, wherein said protic solvent system comprises methanol, ethanol, n-propanol or isopropyl alcohol.

20. A method according to claim 17, wherein said hydrogen peroxide is aqueous, containing about 1% to 99% water by volume.

21. A method according to claim 17, wherein said hydrogen peroxide is aqueous, containing about 2% to 97% water by volume.

22. A method according to claim 17, wherein said hydrogen peroxide is aqueous, containing about 50% to 90% water by volume.

23. A method according to claim 17, wherein said reagent is selected from the group consisting of sodium bicarbonate, potassium bicarbonate, disodium hydrogen phosphate, or trisodium phosphate.

24. A method according to claim 17, wherein one mole equivalent of olefin substrate is combined with more than one mole equivalent of carbodiimide; more than one mole equivalent of mild base; and more than one mole equivalent of hydrogen peroxide.

25. A method according to claim 24, wherein the solvent system is methanol.

26. A method according to claim 17, wherein one mole equivalent of carbodiimide is combined with more than one mole equivalent of olefin substrate; one mole equivalent of mild base; and more than one mole equivalent of hydrogen peroxide.

27. A method according to claim 24, wherein the solvent system is ethanol.

28. A method according to claim 17 further comprising the step of heating said combination.

29. A method according to claim 17, wherein the product of the reaction is an epoxide.

* * * * *

UNITED STATES PATENT AND TRADEMARK OFFICE
CERTIFICATE OF CORRECTION

PATENT NO. : 5,808,115

DATED : Sep. 15, 1998

INVENTOR(S) : Majetich et al.

It is certified that error appears in the above-identified patent and that said Letters Patent is hereby corrected as shown below:

At column 5, line 22, please rewrite "olefins, olefins" as --olefins, and olefins--.

At column 5, line 45, please rewrite "Copper$^{(I)}$" as --Copper (I)--.

At column 10, line 17, please rewrite "didn't" as --did not--.

At column 15, line 22, please rewrite "And this" as --This--.

Signed and Sealed this

Sixth Day of April, 1999

Attest:

Q. TODD DICKINSON

*Attesting Officer*

*Acting Commissioner of Patents and Trademarks*